United States Patent [19]
Bono et al.

[11] Patent Number: 6,129,730
[45] Date of Patent: Oct. 10, 2000

[54] BI-FED OFFSET PITCH BONE SCREW

[75] Inventors: Frank S. Bono, Twinsburg, Ohio; Mark A. Fenton, North Manchester, Ind.

[73] Assignee: Depuy Acromed, Inc., Raynham, Mass.

[21] Appl. No.: 09/247,642

[22] Filed: Feb. 10, 1999

[51] Int. Cl.[7] .................................................. A61B 17/56
[52] U.S. Cl. ................................ 606/73; 606/61; 606/71
[58] Field of Search ............................... 606/73, 71, 72, 606/61; 411/412, 413

[56] References Cited

U.S. PATENT DOCUMENTS

| | | | |
|---|---|---|---|
| 422,307 | 2/1890 | Libbey | 411/412 |
| 2,263,137 | 11/1941 | Oestereicher | 411/412 |
| 4,950,270 | 8/1990 | Bowman et al. | |
| 5,022,277 | 6/1991 | Shaffer | |
| 5,261,910 | 11/1993 | Warden et al. | |
| 5,601,553 | 2/1997 | Trebing et al. | 606/61 |

OTHER PUBLICATIONS

Chapman et al., "Factors Affecting the Pullout Strength of Cancellous Bone Screws," J. Biomechanical Eng., Aug. 1996, vol. 118 (pp. 391–398).

"Fasteners, Materials, and Forming Processes," p. 168, (source and date unknown).

*Primary Examiner*—Michael Buiz
*Assistant Examiner*—Julian W. Woo
*Attorney, Agent, or Firm*—Barnes & Thornburg

[57] ABSTRACT

A bone screw annd assembly are described wherein the bone screw has a dual lead thread that is provided as an offset thread. The bone screw has two leads starting less than 180° apart. Because the leads start less than 180° apart, the leads appear to spiral together along the shaft of the bone screw, creating a large groove and a small groove. The offset dual lead thread of the present invention provides enhanced pullout resistance by overcoming machining limitations to produce a bone screw with increased thread depth while maintaining or decreasing thread pitch. The bone screw may also be provided together with a bone plate to comprise a bone fixation assembly.

23 Claims, 2 Drawing Sheets

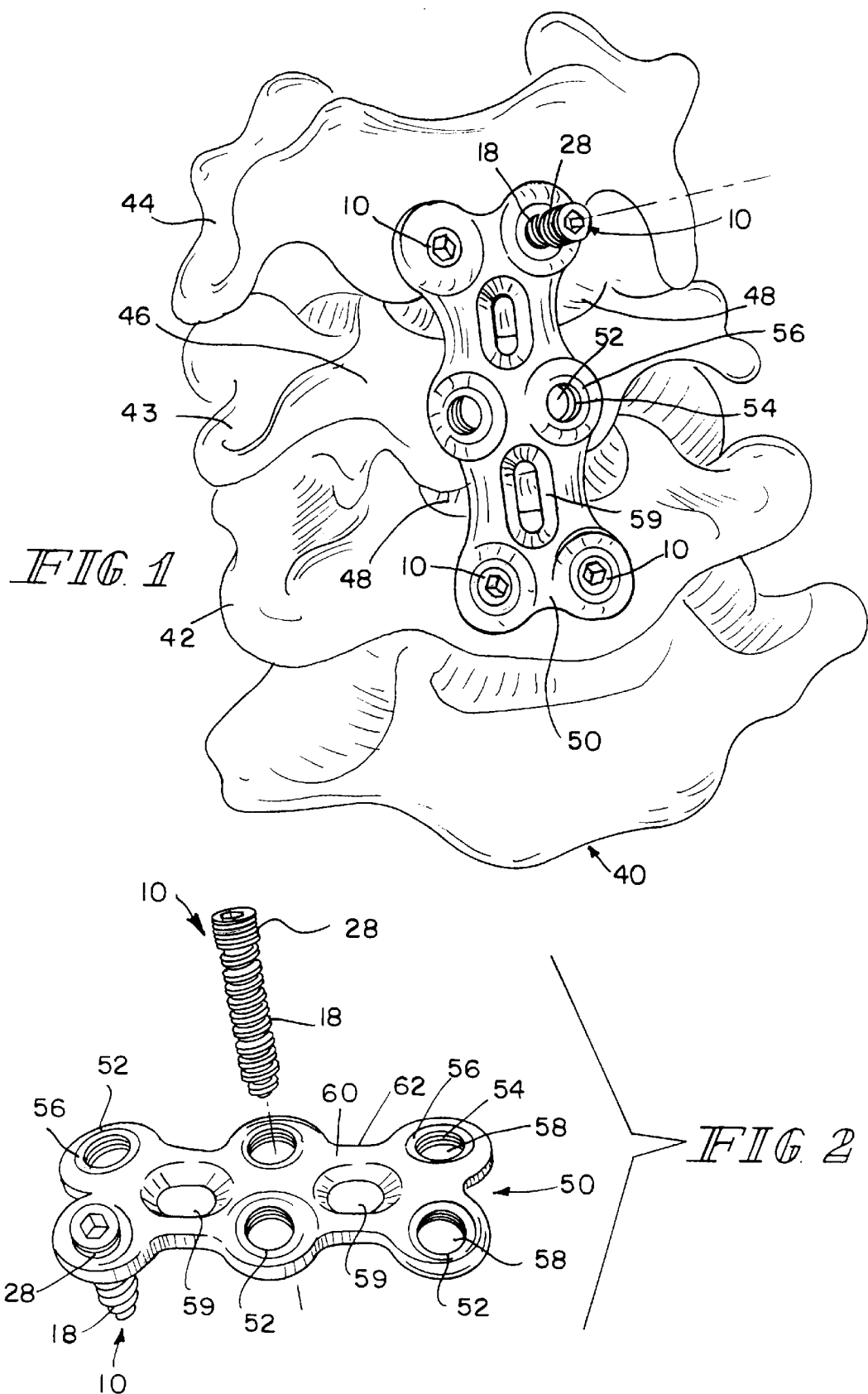

BI-FED OFFSET PITCH BONE SCREW

BACKGROUND AND SUMMARY OF THE INVENTION

The present invention relates to a fastener for coupling a medical device to a bone; more particularly to a bone screw; and most particularly to a bone screw that has a desirable pullout value.

Bone screws have long been known in the art. For example, U.S. Pat. No. 5,261,910 discloses the use of bone screws in conjunction with plates to fix bones into a specific spacial relationship. The methods and materials disclosed in U.S. Pat. No. 5,261,910 are hereby incorporated by reference.

Many prior art bone screws are single thread screws. See, for example, U.S. Pat. No. 4,950,270, hereby incorporated by reference. Such bone screws have a single ridge which travels along the screw in the shape of a helix. Double thread screws are also known. See, for example, U.S. Pat. No. 5,022,277, hereby incorporated by reference. An ordinary double thread screw has two ridges starting 180° apart, both of which form helices along the length of the screw. Triple thread screws, wherein the ridges start 120° apart, are also known. See U.S. Pat. No. 5,022,277.

The present invention comprises a bone screw which has increased pullout resistance by offering an increased thread depth while optimizing thread pitch. The bone screw of the present invention has a dual lead thread which is provided as an offset thread. Unlike ordinary double thread screws, in which the threads start 180° apart, the bone screw of the present invention has two ridges which start closer together, illustratively, about 120° apart. The ridges are provided in a spiral pattern, but appear to spiral together along the shaft of the bone screw, creating a large groove and a small groove. By providing an offset dual lead thread, machining limitations can be overcome to produce a bone screw with increased thread depth while maintaining or decreasing thread pitch, thus providing desirable pullout values.

In an illustrated embodiment, a plate and bone screw apparatus for orthopaedic applications is provided. The bone screw is provided with the offset dual lead and with a second threaded portion adjacent to a head of the bone screw. The plate is provided with a plurality of apertures having internal threads and the threads of the second threaded portion of the bone screw are positioned and sized to engage the internal threads in apertures of the plate. Preferably, the plate is not itself threaded. Rather, internal threads are located on expandable bushings provided within the apertures of the plate. Such a plate is disclosed in U.S. application Ser. No. 08/902,061, filed on Jul. 29, 1997, hereby incorporated by reference. Also, in the preferred embodiment, the shaft of the bone screw in the region of the second threaded portion may be tapered for locking into the expandable bushings.

Additional features of the present invention will become apparent to those skilled in the art upon consideration of the following detailed description of preferred embodiments exemplifying the best mode of carrying out the invention as presently perceived.

BRIEF DESCRIPTION OF THE DRAWINGS

FIG. 1 is a perspective view of a portion of a vertebral column as it would appear to a surgeon during attachment of a bone plate to spaced apart vertebrae, showing the bone plate including apertures, and showing four bone screws in accordance with this invention, in which each bone screw extends through one of the apertures;

FIG. 2 is a perspective view of the bone plate of FIG. 1, showing one bone screw in accordance with the present invention extending through one of the apertures and a second bone screw in general alignment with another of the apertures;

DETAILED DESCRIPTION OF THE DRAWINGS

Figure 3:
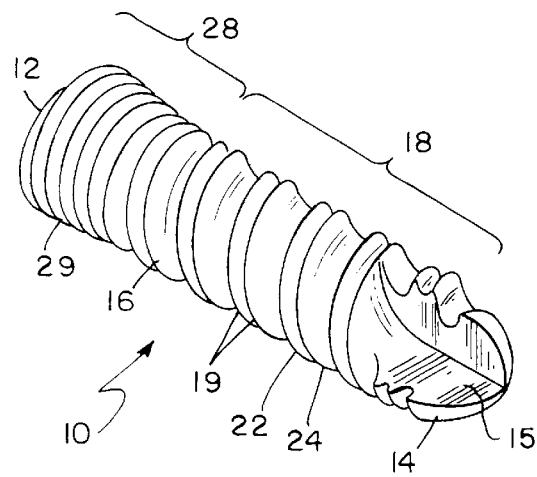
FIG. 3 is a perspective view of a bone screw in accordance with this invention, showing the bone screw including a head, a tip, and a shaft extending between the head and the tip, the shaft having an offset dual lead thread thereon, the dual lead thread including a first ridge and a second ridge spaced apart from the first ridge.

The present invention relates to a bone screw 10 with an offset dual lead thread 19. As representative of the present invention, FIG. 1 illustrates several bone screws 10 of the present invention which are used to couple a bone plate 50 to spaced-apart vertebrae 42, 43, and 44 of a vertebral column 40. Bone screw 10 is provided to couple bone fixation devices to bone and to provide a surgeon with desirable pullout values.

As shown in FIG. 1, bone screw 10 couples bone plate 50 to an anterior side 46 of vertebrae 42, 43, and 44. Vertebrae 42, 43, and 44 are spaced apart by disks 48 or prosthetic spacers (not shown). It is appreciated that bone screw 10 is configured to couple bone plate 50 to an anterolateral or anterior side 46 of cervical, thoracic, or lumbar portions of vertebral column 40 in accordance with the present disclosure. It will be understood that other plates may be used in combination with bone screw 10 in the posterior vertebrae, or elsewhere, such as on the arm, leg, or anywhere bone plates may be used.

Referring now to FIG. 2, bone plate 50 includes an outer surface 60, an inner surface 62 for engaging vertebrae 42, 43, and 44, and apertures 52 extending between outer and inner surfaces 60, 62. As shown in FIG. 2, bone plate 50 has six apertures 52. A bushing 56, having a passageway 58 therethrough with internal threads 54, rides in each aperture 52. Bone plate 50 is also provided with slots 59, which extend between outer and inner surfaces 60, 62. FIG. 2 also shows bone screws 10, sized for extension through apertures 52 of bone plate 50.

Referring now to FIG. 3, bone screw 10 of the present invention includes a head 12, a tip 14, and a shaft 16 extending between head 12 and tip 14. In addition, bone screw 10 has two threaded sections, a dual lead threaded section 18 positioned to extend within bone, and a second threaded section 28 adjacent to head 12. Dual lead threaded section 18 provides desirable pullout values when threaded into vertebrae 42, 43, and 44, while second threaded section 28 is sized to engage internal threads 54 of bushing 56, located within apertures 52 of bone plate 50. Thus, bone screw 10 securely couples bone plate 50 to vertebral column 40. Bone screw 10 is constructed of titanium alloy, although it is understood that bone screw 10 may be constructed of titanium, stainless steel, or any number of a wide variety of materials possessing the mechanical properties suitable for attachment with bone.

While bone screw 10 is described with reference to a particular bone plate 50 and vertebral column 40, it is appreciated that bone screw 10 may be used with any number of prosthetic appliances and in any number of bone sites in accordance with the present disclosure. Additionally, bone screw 10 may be used alone in certain circumstances, without the use of other prosthetic appliances.

Figure 4:
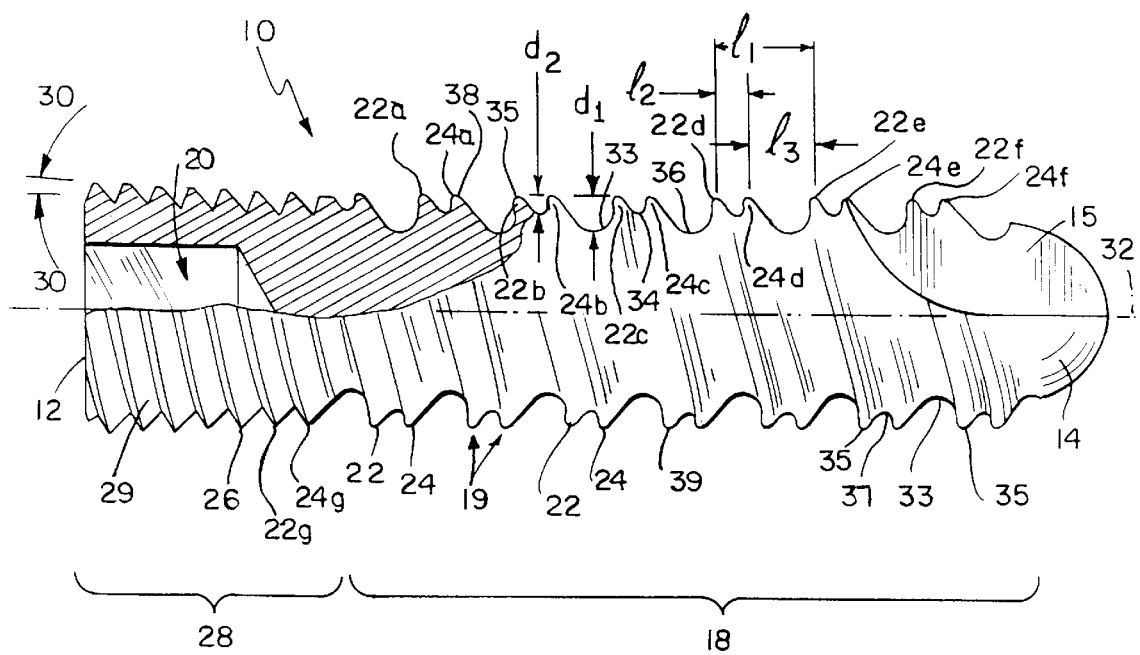
FIG. 4 is a side view of the bone screw of FIG. 3, showing the dual lead thread of the shaft including a first ridge and a second ridge spaced apart from the first ridge.

Referring to FIGS. 3 and 4, dual lead threaded section 18 includes a dual lead thread 19. Dual lead thread 19 comprises a first lead 22 and a second lead 24. Each lead 22, 24 is provided in the form of a helix, which is disposed around shaft 16 along an axis 32. Because dual lead thread 19 is provided as an offset thread, leads 22, 24 appear to spiral together along shaft 16. As shown, bone screw 10 also includes second threaded section 28 located adjacent head 12 of shaft 16. Second threaded section 28 is provided with second thread 29, which is also disposed around shaft 16 along axis 32 in the form of a helix.

As shown in FIG. 4, the leads 22, 24 form a series of adjacent ridges. Referring to positions along a top edge 38 of bone screw 10, a peak 22a of first lead 22 and an adjacent peak 24a of second lead 24 are adjacent to second threaded section 28. Peaks 22a, 24a represent a first turn of dual lead thread 19. Positions indicated by peaks 22b, 24b are separated by one turn along axis 32 of bone screw 10 from the positions indicated by peaks 22a, 24a. Similarly, peaks 22c, 24c are separated by one turn along axis 32 from the positions indicated by peaks 22b, 24b. Peaks 22d, 24d are separated by one turn from peaks 22c, 24c. Also, peaks 22e, 24e and 22f, 24f are similarly separated from adjacent peaks.

First lead 22 has a predetermined lead $1_1$, illustrated as the distance from the position indicated by peak 22c to the position indicated by peak 22d. Second lead 24 is offset from first lead 22 by a predetermined offset 12, illustrated as the distance between the positions indicated by peaks 22c and 24c. Illustratively, first lead 22 and second lead 24 start 120° apart, so that offset 12 is one-third the distance of lead $1_1$. The distance between the position indicated by peak 24c and the next turn of first lead 22, as indicated by peak 22d, offset $1_3$, is two-thirds the distance of lead $1_1$.

Still referring to FIG. 4, bone screw 10 has a large groove 36 and a mall groove 37. Large groove 36 of bone screw 10 has a thread depth $d_1$. Thread depth $d_1$ is the radial distance from a peak position 35 to a position at a trough 33 of lead $1_3$. Small groove 37 has a thread depth $d_2$, which is the radial distance from peak position 35 to a position at a trough 34 of lead $1_2$. In the illustrative embodiment, thread depth $d_1$ is at least twice thread depth $d_2$.

To achieve a desirable pullout value in cancellous bone, bone screw 10 maximizes thread depth. Using currently available standard machining techniques to achieve the greatest possible thread depth, the average of $d_1$ and $d_2$ would be greater on bone screw 10 with offset dual lead threaded section 18 than the thread depth obtained in machining a bone screw with the same length, major diameter, and with an ordinary double thread having lead $1_1$. Thus, in manufacturing bone screw 10, average thread depth can be increased while maintaining or even decreasing thread pitch. Because bone screw 10 of this invention has increased thread depth, it may provide greater pullout values than a screw with an ordinary double thread having the same length, major diameter, and lead $1_1$.

Bone screws having an offset dual lead thread in which the offset is other than 120° may also provide desirable pullout values and are within the scope and spirit of the invention. For example, an offset of 90° would correspond to two adjacent leads of a quadruple lead thread, while 144° would correspond to the first and third leads of a quintuple lead thread. Both of these examples, and others, may provide desirable pullout values. Offsets between about 90° and about 150° may be effective in providing desirable pullout values.

Figure 5:
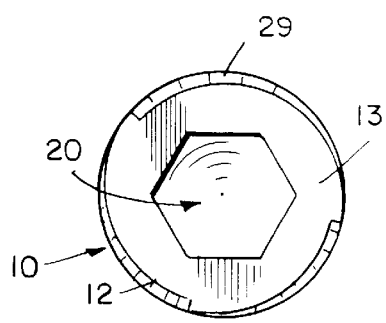
FIG. 5 is a top view of the bone screw of FIG. 3, showing the head including an hexagonal-shaped aperture.

FIG. 5 shows head 12 of bone screw 10. As illustrated, head 12 includes a surface 13 which is formed to include a cavity 20 for receiving a driving device (not shown). While cavity 20 of bone screw 10 is generally hexagonal in shape, it will be appreciated that other head configurations for use with other driving devices may be provided in accordance with the present disclosure.

As shown in FIGS. 3 and 4, tip 14 is provided with cutting edge 15. Thus, bone screw 10 is self-tapping. While the preferred embodiment is for a self-tapping bone screw, it is understood that bone screws with tips of other configurations may be used in accordance with this invention.

As best seen in FIGS. 4, second threaded section 28 lies adjacent to head 12. As illustrated, second thread 29 is a triple thread, with leads starting about 120° apart. First lead 22 and second lead 24 of dual lead thread 19 continue through second threaded section 28, and they are joined by a third lead 26, to form second thread 29. In FIG. 4, a peak 22g indicates a position on a bottom edge 39 of bone screw 10. Peak 22g is located along first lead 22 within second threaded section 28. Similarly, the position indicated by peak 24g is located along second lead 24 within second threaded section 28. Third lead 26 is positioned about 120° from first lead 22 and about 120° from second lead 24. While dual lead threaded section 18 is designed for providing desirable pullout values, second threaded section 28 is provided for securing other bone stabilization devices, such as bone plate 50, shown in FIG. 2. As illustrated, second threaded section 28 is designed to engage internal threads 54 of bushing 56 of bone plate 50, to secure bone plate 50 to a bone. While illustratively second threaded section 28 is a triple lead thread, it is understood that thread pitch, number of leads, and spacing may vary in accordance with the present invention.

Still referring to FIG. 4, second threaded section 28 of shaft 16 tapers, as shown by a tapered angle 30, such that shaft 16 is slightly wider adjacent to head 12. In the preferred embodiment, tapered angle 30 may be about two to about twelve degrees. As illustrated, tapered angle 30 is approximately six degrees.

To use bone screw 10 of this invention with bone plate 50, the surgeon first positions bone plate 50 on vertebral column 40. Tip 14 of bone screw 10 is inserted into passageway 58 of bushing 56. As bone screw 10 enters passageway 58, internal threads 54 on bushing 56 receive dual lead threaded section 18 and internal threads 54 guide tip 14 through passageway 58. The surgeon uses an insertion tool (not shown) in hexagonal cavity 20 of bone screw 10 to rotate bone screw 10 within passageway 58, to advance bone screw 10 through bone plate 50. Once tip 14 exits passageway 58, tip 14 engages vertebral column 40 and begins to thread into one of the vertebrae, for example, first vertebra 42. Because tip 14 is self-tapping, bone screw 10 cuts its own threads in first vertebra 42. Thread depths $d_1$ and $d_2$, in part, provide the desired pullout values.

Continued rotation of bone screw 10 advances bone screw 10 such that second thread 29 engages internal threads 54. Tapered angle 30 of second threaded section 28 of shaft 16 expands bushing 56 and presses bushing 56 into frictional locking engagement with bone plate 50. As bone screw 10 is driven further into vertebral column 40 and through bone plate 50, second threaded section 28 causes bushing 56 to expand, creating a friction lock between bone plate 50 and bushing 56, thereby locking bone screw 10 into bone plate 50. If desired, prior to insertion of bone screw 10, a drill guide (not shown) may be used to drill a pilot hole (not shown) in vertebral column 40.

It will be understood that various applications may require other head configurations and some applications may not require second threaded section 28. For example, a bone screw with an alternative head configuration may extend through slot 59 to secure disk replacement material (not shown) to bone plate 50. Bone screws with alternative head configurations are within the scope and spirit of this invention.

Although the invention has been described in detail with reference to a preferred embodiment, variations and modifications exist within the scope and spirit of the invention as described and defined in the following claims.

What is claimed is:

1. A bone screw comprising:
    a head, a tip, and a shaft extending between the head and the tip, the shaft including a dual lead threaded section, the dual lead threaded section having a first lead and a second lead each in the form of helix, wherein the second lead starts between about 90° and 150° after the first lead.

2. The bone screw of claim 1, wherein the second lead starts about 120° after the first lead.

3. The bone screw of claim 2, wherein the shaft includes a second threaded section extending between the dual lead threaded section and the head.

4. The bone screw of claim 3, wherein the second threaded section comprises a triple lead thread.

5. The bone screw of claim 1 wherein the tip includes a cutting edge.

6. The bone screw of claim 1 wherein the dual lead threaded section further includes a first thread groove and a second thread groove, and the first thread groove has a depth which is greater than a depth of the second thread groove.

7. A bone fixation assembly comprising:
    a bone plate having a plurality of apertures, and
    a bone screw including a head, a tip, and a shaft extending between the head and the tip along an axis,
    the shaft having a dual lead threaded section adjacent the tip, the dual lead threaded section having a dual lead thread disposed around the shaft along the axis, the dual lead thread having first lead and a second lead, wherein the second lead starts less than 180° after the first lead, and the shaft having a second threaded section extending between the dual lead threaded section and the head.

8. The assembly of claim 7 wherein the apertures are internally threaded, and the second threaded section of the shaft is threaded to engage the internally threaded apertures.

9. The assembly of claim 8 wherein the second lead starts approximately 120° after the first lead.

10. The assembly of claim 7, further comprising internally threaded expandable bushings, wherein the bushings ride in the apertures of the bone plate, the second threaded section of the shaft has threads to engage the internally threaded expandable bushings, and the second threaded section of the shaft tapers to be wider closer to the head.

11. The assembly of claim 10 wherein the second lead starts approximately 120° after the first lead, the threads of the second section are disposed around the shaft to form a triple lead thread, and the dual lead thread of the first section and the triple lead thread of the second section are sized to engage the internal threads of the expandable bushings.

12. The assembly of claim 7 wherein the dual lead threaded section includes a first thread depth located adjacent to the first lead and provided axially toward the head from the first lead, and a second thread depth located adjacent the second lead and provided axially toward the head from the second lead, wherein the first thread depth is greater than the second thread depth.

13. A bone fixation assembly comprising:
    an implantable medical device and
    a bone screw having a head, a tip, and a shaft extending between the head and the tip, the shaft having a first section adjacent to the tip and a second section extending between the first section and the head, the first section having a dual lead thread disposed about the shaft, the dual lead thread having a first lead and a second lead, wherein the second lead starts less than 180° from the first lead, and the second section is designed to engage the implantable medical device.

14. An assembly of claim 13, wherein the implantable medical device is selected from the group consisting of plates, rods, and hooks.

15. An assembly of claim 14, wherein the second lead starts between about 90° to about 150° from the first lead.

16. An assembly of claim 15, wherein the second lead starts about 120° from the first lead.

17. An assembly of claim 13, wherein the first section is further provided with a large groove and a small groove disposed around the shaft between the leads, and the large groove is deeper than the small groove.

18. A bone screw comprising:
    a head, a tip, and a shaft extending between the head and the tip, the shaft including a dual lead threaded section, the dual lead threaded section having a first lead and a second lead each in the form of a helix, wherein the second lead starts about 120° after the first lead.

19. The bone screw of claim 18, wherein the shaft includes a second threaded section extending between the dual lead threaded section and the head.

20. The bone screw of claim 19, wherein the second threaded section comprises a triple lead thread.

21. The bone screw of claim 18, wherein the tip includes a cutting edge.

22. The bone screw of claim 18, wherein the dual lead threaded section further includes a first thread groove and a second thread groove, and the first thread groove has a depth which is greater than the depth of the second thread groove.

23. The bone screw of claim 18, wherein the bone screw is comprised of a titanium alloy.

* * * * *

US006129730C1

(12) EX PARTE REEXAMINATION CERTIFICATE (4941st)
United States Patent
Bono et al.

(10) Number: US 6,129,730 C1
(45) Certificate Issued: May 25, 2004

(54) BI-FED OFFSET PITCH BONE SCREW

(75) Inventors: Frank S. Bono, Twinsburg, OH (US); Mark A. Fenton, North Manchester, IN (US)

(73) Assignee: Depuy Acromed, Inc., Cleveland, OH (US)

Reexamination Request:
No. 90/006,123, Oct. 3, 2001

Reexamination Certificate for:
Patent No.: 6,129,730
Issued: Oct. 10, 2000
Appl. No.: 09/247,642
Filed: Feb. 10, 1999

(51) Int. Cl.[7] ............................................. A61B 17/56
(52) U.S. Cl. ............................... 606/73; 606/61; 606/71
(58) Field of Search ............................... 606/61, 71, 72, 606/73, 70; 411/412, 413; 433/174

(56) References Cited

U.S. PATENT DOCUMENTS 4,103,422 A    8/1978    Weiss et al.

FOREIGN PATENT DOCUMENTS

| DE | 43 29 788 A1 | 3/1995 |
| EP | 0 377 068 A | 7/1990 |
| FR | 2 766 353 | 1/1999 |
| GB | 2 252 381 A | 8/1992 |
| WO | WO 97/46167 | 12/1997 |

*Primary Examiner*—Eduardo C. Robert

(57) ABSTRACT

A bone screw annd assembly are described wherein the bone screw has a dual lead thread that is provided as an offset thread. The bone screw has two leads starting less than 180° apart. Because the leads start less than 180° apart, the leads appear to spiral together along the shaft of the bone screw, creating a large groove and a small groove. The offset dual lead thread of the present invention provides enhanced pullout resistance by overcoming machining limitations to produce a bone screw with increased thread depth while maintaining or decreasing thread pitch. The bone screw may also be provided together with a bone plate to comprise a bone fixation assembly.

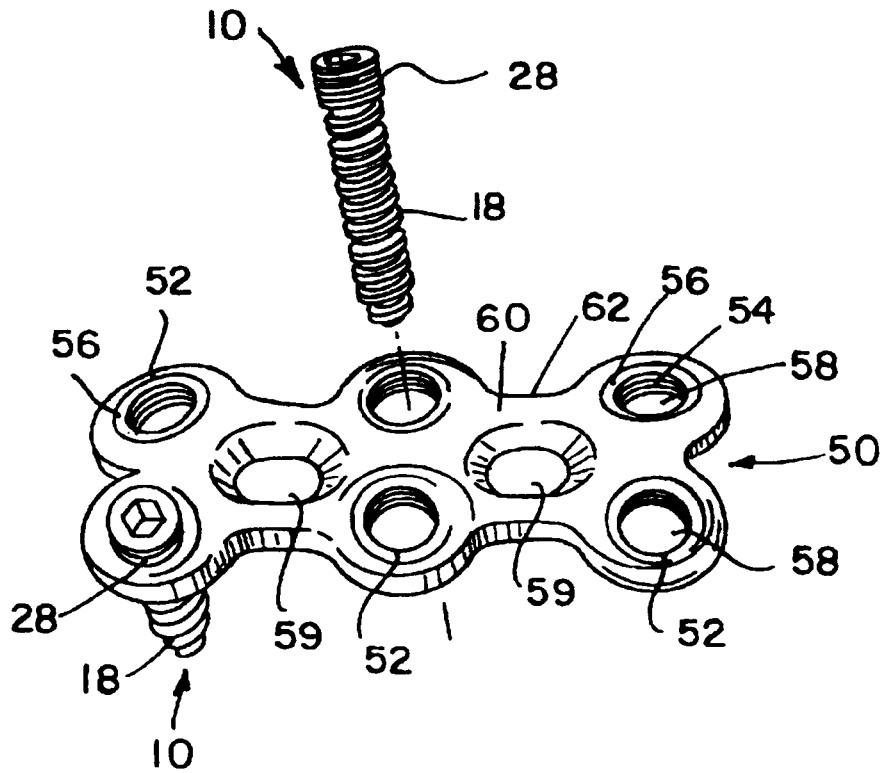

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 7–12 is confirmed.

Claims 1–3, 5, 6, 13, 17–19 and 21–23 are cancelled.

Claims 4, 14 and 20 are determined to be patentable as amended.

Claims 15 and 16, dependent on an amended claim, are determined to be patentable.

4. [The] *A* bone screw [of claim 3, wherein] *comprising:*

*a head, a tip, and a shaft extending between the head and the tip, the shaft including a dual lead threaded section, the dual lead threaded section having a first lead and a second lead each in the form of helix, wherein the second lead starts about 120° after the first lead, the shaft includes a second threaded section extending between the dual lead threaded section and the head, and the* second threaded section comprises a triple lead thread.

14. [An] *A bone fixation* assembly [of claim 13, wherein] *comprising:*

*an implantable medical device and*

*a bone screw having a head, a tip, and a shaft extending between the head and the tip, the shaft having a first section adjacent to the tip and a second section extending between the first section and the head, the first section having a dual lead thread disposed about the shaft, the dual lead thread having a first lead and a second lead, wherein the second lead starts less than 180° from the first lead, the second section is designed to engage the implantable medical device, and the* implantable medical device is selected from the group consisting of plates, rods, and hooks.

20. [The] *A* bone screw [of claim 19, wherein] *comprising:*

*a head, a tip, and a shaft extending between the head and the tip, the shaft including a dual lead threaded section, the dual lead threaded section having a first lead and a second lead each in the form of a helix, wherein the second lead starts about 120° after the first lead, wherein the shaft includes a second threaded section extending between the dual lead threaded section and the head, and* the second threaded section comprises a triple lead thread.

\* \* \* \* \*